United States Patent [19]

Schneider

[11] 3,988,328
[45] Oct. 26, 1976

[54] 5-AMINO-2,3,7,8-TETRATHIAALKANE-1,9-DIOIC ACIDS, ESTERS AND SALTS

[75] Inventor: Rupert Schneider, Riehen, Switzerland

[73] Assignee: Sandoz Ltd., Basel, Switzerland

[22] Filed: Aug. 20, 1974

[21] Appl. No.: 498,956

[30] Foreign Application Priority Data
Aug. 27, 1973 Switzerland.................... 12247/73

[52] U.S. Cl. ............... 260/247.1 R; 260/268 R; 260/293.73; 260/293.85; 260/326.42; 260/479 S; 260/481 R; 260/501.21; 260/534 S; 260/561 A; 260/562 N; 71/88; 71/92; 71/94; 71/95; 71/98
[51] Int. Cl.² ............... C07D 295/74; C07C 149/20
[58] Field of Search ............ 260/247.1 R, 268 R, 260/293.73, 293.85, 326.42

[56] References Cited
UNITED STATES PATENTS

| | | | |
|---|---|---|---|
| 3,318,936 | 5/1967 | Sakai | 260/247.1 R |
| 3,332,943 | 7/1967 | Konishi | 260/247.1 R |
| 3,711,477 | 1/1973 | Schelling | 260/247.1 R |

OTHER PUBLICATIONS
Belgian Patent Publication 780,225, (1972).
Audus, The Physiology and Biochemistry of Herbicides, (1964).

Primary Examiner—Lorraine A. Weinberger
Assistant Examiner—Michael Shippen
Attorney, Agent, or Firm—Gerald D. Sharkin; Richard E. Vila

[57] ABSTRACT

The present invention concerns novel 2-dialkylamino propane derivatives of the formula:

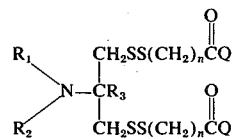

wherein either, $R_1$ and $R_2$ are each alkyl; $R_3$ is hydrogen or alkyl; Q is —OM, wherein M is hydrogen or a cation, —$OR_4$, wherein $R_4$ is alkyl or unsubstituted or substituted phenyl or —$NR_5R_6$, wherein $R_5$ is hydrogen, alkyl or unsubstituted or substituted phenyl and $R_6$, independently has one of the significances of $R_5$ or is —$NHR_7$, wherein $R_7$ is hydrogen and n is an integer 1, 2 or 3, in free base or acid addition salt form.

The compounds possess plant growth regulating and herbicidal properties and are accordingly useful in agriculture.

19 Claims, No Drawings

5-AMINO-2,3,7,8-TETRATHIAALKANE-1,9-DIOIC ACIDS, ESTERS AND SALTS

The present invention relates to 2-dialkylamino propane derivatives and more specifically to 2-dialkylamino propane, 1,3-disubstituted by dithialkylacyl groups, indicated for agricultural use as plant growth regulators and herbicides.

Accordingly, the present invention provides compounds of formula I, $$R_1\diagdown\phantom{N}\diagup CH_2SS(CH_2)_nCQ \\ \phantom{xxx}N-CR_3 \\ R_2\diagup\phantom{N}\diagdown CH_2SS(CH_2)_nCQ$$
(with C=O groups)     I wherein either, $R_1$ and $R_2$ are each, independently, alkyl ($C_1$–$C_5$), or, $R_1$ and $R_2$, together with the nitrogen atom to which they are bound, form a 5 or 6 membered nitrogen containing heterocyclic ring which apart from the nitrogen atom may contain a further hetero atom, e.g. nitrogen or oxygen, $R_3$ is hydrogen or alkyl ($C_1$ or $C_2$), Q is —OM
  wherein M is hydrogen or a cation,
—$OR_4$
  wherein $R_4$ is alkyl ($C_1$—$C_8$), phenyl, or phenyl substituted by halogen, nitro, alkoxy ($C_1$–$C_5$), phenoxy, carboxy, alkoxycarbonyl ($C_2$—$C_6$) and/or carboxamido or
—$NR_5R_6$
  wherein $R_5$ is hydrogen, alkyl ($C_1$–$C_5$), phenyl or phenyl substituted by halogen, nitro, alkoxy ($C_1$–$C_5$), phenoxy, carboxy, alkoxycarbonyl ($C_2$–$C_6$) and/or carboxamido
  and $R_6$, independently, has one of the significances of $R_5$ or is —$NHR_7$
    wherein $R_7$ is hydrogen or alkyl ($C_1$–$C_5$)
and $n$ is an integer 1, 2 or 3,
in free base of acid addition salt form.

By the term "halogen" as employed herein is meant fluorine, chlorine or bromine, preferably fluorine or chlorine, especially chlorine.

When any of $R_1$, $R_2$, $R_3$, $R_4$, $R_5$, $R_6$ and $R_7$ are or contain an alkyl group (e.g. alkoxy), this may be straight or branched chain, primary, secondary or tertiary. Preferably such alkyl or alkyl containing groups contain 1 to 4, more preferably 1 to 3 carbon atoms, e.g. methyl, ethyl or n-propyl.

When $R_1$ and $R_2$, together with the nitrogen atom to which they are bound, form a 5 or 6 membered heterocyclic ring, such ring may be saturated or unsaturated, preferably saturated, and may contain a further heteroatom such as oxygen or nitrogen. Preferred rings are of the formula $$-N\diagup\diagdown X$$
(6-membered ring)

wherein X is oxygen, —NH—, —$CH_2$— or a direct covalent bond, preferably oxygen, —$CH_2$— or a direct covalent bond, i.e. piperidino, pyrrolidino or morpholino.

When any of $R_4$, $R_5$ or $R_6$ are substituted phenyl, preferably the phenyl radical is substituted by 1 to 3 substituents, more preferably by 1 or 2 substituents, e.g. 1 substituent, selected from halogen, nitro, alkoxy ($C_1$–$C_5$), phenoxy, carboxy, alkoxycarbonyl ($C_2$–$C_6$) and carboxamido.

When M is a cation, preferably this is an alkali metal, especially potassium or sodium, or the ammonium cation.

The present invention also provides a process for the production of a compound of formula I, which comprises a. condensing a compound of formula II, $$R_1\diagdown\phantom{N}\diagup CH_2-S-X_1 \\ \phantom{xxx}N-C-R_3 \\ R_2\diagup\phantom{N}\diagdown CH_2-S-X_1$$
    II wherein $R_1$, $R_2$ and $R_3$ are as defined above and
each $X_1$ is a leaving group or is potassium or sodium,
with a compound of formula III, $$X_2-S(CH_2)_nC-Q$$
(with C=O)     III wherein n and Q are as defined above and
$X_2$ is a leaving group or is potassium or sodium,
with the proviso that both $X_1$'s are leaving groups and $X_2$ is sodium or potassium, or both $X_1$'s are sodium or potassium and $X_2$ is a leaving group or
b. condensing a compound of formula Ia, $$R_1\diagdown\phantom{N}\diagup CH_2-SS(CH_2)_nC-Q_1 \\ \phantom{xxx}N-C-R_3 \\ R_2\diagup\phantom{N}\diagdown CH_2-SS(CH_2)_nC-Q_1$$
    Ia wherein $R_1$, $R_2$, $R_3$ and $n$ are as defined above and
$Q_1$ is a group —$OR_4$
  wherein $R_4$ is as defined above,
with a compound of formula IV, $$H-Q_2$$     IV wherein $Q_2$ is a group —OM
  wherein M is as defined above
or —$NR_5R_6$
  wherein $R_5$ and $R_6$ are as defined as above,
to produce a compound of formula Ib, $$R_1\diagdown\phantom{N}\diagup CH_2-SS(CH_2)_nC-Q_2 \\ \phantom{xxx}N-C-R_3 \\ R_2\diagup\phantom{N}\diagdown CH_2SS(CH_2)_nC-Q_2$$
    Ib wherein $R_1$, $R_2$, $R_3$, $n$ and $Q_2$ are as defined above.

In process variant (a), when each $X_1$ of formula II is a leaving group, preferred leaving groups are the group —$SO_2R_8$ wherein $R_8$ is aryl ($C_6$–$C_{12}$), preferably tolyl or phenyl, and the group
—$SO_3M'$
wherein $M'$ is potassium or sodium.

Alternatively when $X_2$ of formula III is a leaving group, preferred leaving groups are chlorine and the group

—$SO_2R_8$ wherein $R_8$ is as defined above.

The reaction conditions employed in process (a) will to a large extent depend on the nature of the leaving group in the compounds of formulae II or III.

For example, when each $X_1$ is the leaving group —$SO_2R_8$, then the reaction may be effected as follows.

The compounds II and III are preferably dissolved in an anhydrous organic solvent or solvent mixture such as an alcohol, e.g. methanol, ethanol and isopropanol or a nitrile, e.g. acetonitrile, preferably anhydrous methanol. The reaction is preferably allowed to proceed initially at room temperature, e.g. for 1 to 2 hours. Subsequently it is preferred that the reaction mixture is subjected to mild heating, e.g. in the range 25° to 50°C, over a period of, e.g. 1 to 2 hours. Preferably the reaction mixture is stirred.

When each $X_1$ is the leaving group —$SO_3M'$, then the reaction may, for example, be effected as follows viz.

The compound of formula II, suitably in a solvent such as water, is preferably added, over the course of, for example, compound 15 minutes, to the compounds of formula III dissolved in a solvent, e.g. water. Preferably, the reaction medium comprises a two phase system consisting of an aqueous buffer solution having a pH of about 8, the pH being maintained by the addition of mineral acid, preferably hydrochloric acid, and a water immiscible solvent such as ether, benzene, toluene, methylene chloride and chloroform, preferably the latter two. Preferably, the aqueous buffer phase is saturated with a suitable salt, e.g. sodium chloride and/or other reagents such as formaldehyde, for the purposes of removing and/or binding the sodium sulphite formed during the reaction. The mixture is preferably stirred only for a relatively short period, e.g. 5 to 10 minutes.

When $X_2$ is the leaving group $R_8SO_2$, then the reaction may, for example, be effected as follows viz.

The compound of formula II, preferably freshly prepared, is preferably dissolved in a suitable anhydrous organic solvent, e.g. anhydrous acetonitrile or chloroform, and the compound of formula III, preferably dissolved in a suitable anhydrous organic solvent, e.g. anhydrous acetonitrile or chloroform, added thereto. Preferably the reaction mixture is maintained at room temperature and stirred.

When $X_2$ is the leaving group —Cl, then the reaction may, for example, be effected as follows viz:

The compound of formula II, preferably freshly prepared, is preferably dissolved in an appropriate anhydrous organic solvent or solvent mixture, e.g. anhydrous chloroform or carbon tetrachloride, and the compound of formula III preferably dissolved in an anhydrous organic solvent or solvent mixture, e.g. chloroform or carbon tetrachloride, added thereto. The reaction is preferably effected with stirring, over a period of, e.g., 1 to 3 hours. Preferably the reaction is effected in an inert atmosphere, e.g. nitrogen or argon.

In general, working up may be effected in manner known per se.

The reaction conditions, e.g. solvents and temperatures, employed in process b), will also, to a large extent depend on the exact significance of $Q_2$ in formula IV.

Thus, when $Q_2$ is a group —OM, the saponification may be effected in manner known per se by acid catalysed hydrolysis of the compound of formula Ia. The reaction is accordingly preferably effected by dissolving the compound of formula Ia in a dilute aqueous mineral acid, e.g. 1N sulphuric acid, and heating the reaction mixture, conveniently to 100°C, over a period of between, e.g. 4 to 5 hours. When salt forms are required, the resulting compound may be reacted with an appropriate base.

When $Q_2$ is a group —$NR_5R_6$, then the amidation may be effected by aminolysis with a compound of formula $HNR_5R_6$ in an appropriate solvent, e.g. acetonitrile, dimethyl formamide, benzene or toluene.

In general, working up may be effected in manner known per se.

The compounds of formulae II and III are either known or may be produced in manner known per se.

Thus, the compounds of formula II, wherein each $X_1$ is the leaving group —$SO_2R_8$ or —$SO_3M'$, may be produced by reacting a compound of formula V, $$\begin{array}{c} R_1 \\ \phantom{R}\diagdown \\ \phantom{RR}N-C-R_3 \\ \phantom{R}\diagup \\ R_2 \end{array} \begin{array}{c} CH_2-Hal \\ \diagup \\ \diagdown \\ CH_2-Hal \end{array} \qquad V$$

wherein $R_1$, $R_2$ and $R_3$ are as defined above and Hal is halogen, preferably chlorine,
with a compound of formula VI, $$M'SSO_2R_8 \qquad VI$$

wherein $M'$ and $R_8$ are as defined above,
or with potassium or sodium thiosulphate pentahydrate respectively.

The reaction is preferably effected an appropriate solvent, e.g. 50% aqueous methanol, with heating up to the boiling temperature, e.g. 100°C. If desired, the resulting compound may be employed directly in process variant (a) above, e.g., after extraction with an appropriate water immiscible solvent, e.g. ether, benzene, toluene, methylene chloride or chloroform, preferably the latter two. Alternatively, the compound of formula I may be isolated, working up being effected in conventional manner.

In addition, the compounds of formula II, wherein each $X_1$ is a potassium or sodium cation may be produced from a compound of formula VII, $$\begin{array}{c} R_1 \\ \phantom{R}\diagdown \\ \phantom{RR}N-C-R_3 \\ \phantom{R}\diagup \\ R_2 \end{array} \begin{array}{c} O \\ \parallel \\ CH_2-S-C-CH_3 \\ \\ O \\ \parallel \\ CH_2-S-C-CH_3 \end{array} \qquad VII$$

wherein $R_1$, $R_2$ and $R_3$ are as defined above,
by solvolysis with a sodium or potassium metal alcoholate in the corresponding alcohol, e.g. the methanolate or ethanolate in methanol or ethanol, preferably with heating, conveniently under reflux. Preferably the reaction is effected in an inert atmosphere, e.g. nitrogen or argon. After removal of the resulting acetic ester and excess solvent by distillation, preferably in an inert atmosphere, the resulting product may be employed directly in process variant a) described above.

Further, the compound of formula III, wherein $X_2$ is chlorine may be produced, for example, by reacting a compound of formula VIII,

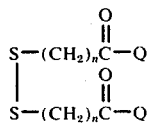

wherein n and Q are as defined above,
with chlorine or thionyl chloride in an appropriate solvent such as carbon tetrachloride or chloroform, with stirring and cooling to below room temperature, e.g. to $-20°$ to $-30°$ C, conveniently in the absence of direct sunlight.

The compounds of formulae IV, V, VI, VII and VIII are either known or may be produced in manner known per se.

In view of the presence of a basic nitrogen atom, the compounds of formula I may exist in free base or acid addition salt forms. Reference to compounds of formula I herein is intended to embrace all such forms.

Acid addition salt forms of the compounds of formula I may be produced from free base forms, e.g. by reaction with an appropriate acid, in manner known per se and vice versa.

Examples of acids suitable for acid addition salt formation are organic acids such as oxalic acid and inorganic acids such as hydrochloric acid.

The compounds of formula I are colourless or slightly yellow oils or crystals which may be characterised by their Rf values and/or melting points. Generally, they are readily soluble in polar solvents, e.g. alcohols and nitriles, the compounds of formula I, wherein Q is —OM being generally well soluble in water.

The compounds of formula I possess plant growth regulating properties and are accordingly indicated for use in agriculture as plant growth regulators.

By the term "plant growth regulating properties" is meant not only growth stimulating or retarding effects in such plant development processes as blossoming, seeding, fruitation, leafdrop, germination, sprouting and shoot formation but also other changes in the development of plant growth such as the known auxin effects, e.g. bending or thickening of the plant parts, e.g. leaves and/or stems, or colour changes in the leaves, blossoms or fruit.

Thus valuable uses to which plant growth regulators may be applied include inter alia defoliation, accelerated maturity, reduction of fruit set, retardation of blossom, prolongation of the harvesting period and increased storage stability of the harvested crop or fruit. Plants to which such plant growth regulating activity may be applied are ornamentals, crops such as cotton, hemp, nape, sunflower, maize, corn, tomatoes and vegetables, and in fruit and berry bearing growth.

Apart from their plant growth regulating effects, the compounds also possess herbicidal properties and are accordingly indicated for use as herbicides, especially at higher rates of application.

For use as plant growth regulators and also as herbicides, the compounds are preferably employed for storage and application purposes in the form of a composition in association with a plant growth regulator or herbicide carrier and/or diluent. Such compositions may be either in liquid or solid forms, preferably the former.

Liquid concentrate forms, e.g. emulsion concentrates, i.e. for storage and trade purposes, may comprise solutions of the compound in a solvent of comparatively low boiling point, especially alcohols, e.g. ethyl alcohol, isopropanol or methyl cyclohexanol, ketones, e.g. acetone or cyclohexanone, hydrocarbons, e.g. toluene or xylene, and/or chlorinated hydrocarbons, e.g. tetrachloroethane, ethylene chloride or trichloroethylene. The concentrates may further include surfactants, if necessary, to improve the water solubility or emulsion forming properties of the compounds of formula I. Examples of surfactants are cationic surfactants such as quaternary ammonium compounds, anionic surfactants such as soaps, long chain aliphatic sulphuric acid mono-esters and salts of long chain alkoxyacetic acids, and non-ionic surfactants such as polyethylene ethers of fatty alcohols, polyoxyethylene condensation products or particularly, alkaryl polyglycol ethers, e.g. isooctylphenyldecaglycol ether or nonylphenyleikosaglycol ether.

Liquid application forms of the compounds of formula I may be produced by diluting the abovementioned concentrate forms with water to the desired concentration.

Solid concentrate or application composition forms of the compounds, e.g. dusting, strewing or granulate forms, may be produced by grinding or otherwise mixing the compounds with suitable solid carrier materials. Examples of solid carrier materials are kaolin, talc, chalk, limestone and cellulose powders. Apart from carrier materials, adjuvants may be incorporated into the solid forms such as surfactants, e.g. to improve the adhesive properties of the composition with respect to the treated plants and to improve wettability or dispersibility thereof.

Plant growth regulator or herbicidal compositions may, for example, contain from 1 to 90 %, preferably from 2 to 80 % by weight of the compound in concentrate forms, and between 0.01 and 10 % by weight of the compound in application forms.

The compounds of formula I are applied to the locus to be treated in sufficient amount to exert the desired action. The exact amount of compound applied will vary depending on, for example, the specific compound employed, the desired result, ambient conditions and the plant species to be treated. In general, however, a plant growth regulating effect, e.g. defoliation, may be obtained when applied to a plant locus in an amount in the range 0.1 to 5.0 kg/hectare while a herbicidal effect may be obtained when applied to a plant or weed locus in an amount in the range 5.0 to 30 kg/hectare, i.e. a plant growth regulating effect is generally observed at lower application rates while a herbicidal effect is generally observed at higher application rates.

Two examples of emulsifiable concentrate forms of the compounds of the invention are described below.

Emulsifiable concentrate (i)

10 parts by weight of a compound of formula I, e.g. 5-dimethylamino-2,3,7,8-tetrathianonane-1,9-dioic acid dissolved in 80 parts by weight of isopropanol and 10 parts by weight of isooctylphenyldecaglycol are added thereto as emulsifying agent.

The concentrate is diluted with water to the desired extent for application purposes.

Emulsifiable concentrate (ii)

25 parts by weight of a compond of formula I, e.g. dimethyl-(5-morpholino)-2,3,7,8-tetrathianonane-1,9-dioate dissolved in 50 parts by weight of acetone and 25 parts by weight of nonylphenyleikosaglycol ether are added thereto as emulsifying agent.

The concentrate is diluted with water to the desired extent for application purposes.

The plant growth regulating and herbicidal properties of the compounds of formula I are indicated in the following Tests A, B and C.

TEST A: Determination of germination rate, sprout and root growth (cell elongation and cell division) in cucumbers (Cucumis sativus L)

Cucumber seeds are placed on a nybolt net of appropriate mesh size. The net touches the surface of a Knop nutrient solution in a plastics cup containing the active agents to be tested in doses of 125 p.p.m. (or 12.5 p.p.m., marked with $^+$). 16 Seeds are used for each cup. The germination rate is determined, the longitudinal growth of the sprouts and roots is measured and other growth effects are visually determined after 7 days in comparison with control plants (control plant = 100%.

The results are set out in Table 1 below.

| Active agent of general formula I | Germination | | Sprout length in % Compared without untreated control plants after | Root length | Other effects |
|---|---|---|---|---|---|
| | 1 | 7 | 7 days | 7 | |
| a) Diethyl-(5-dimethylamino)-2,3,7,8-tetrathianonane-1,9-dioate | 108$^+$ | 87$^+$ | 50$^+$ | 63$^+$ | sprout G1 |
| b) Hydrogenoxalate of a) | 50$^+$ | 80$^+$ | 50$^+$ | 50$^+$ | sprout G1A |
| c) Dimethyl-(5-dimethyl-amino)-2,3,7,8-tetrathianonane-1,9-dioate | 100 | 87 | 29 | 29 | sprout G1 root HB |
| d) Hydrogenoxalate of c) | 90 | 100 | 43 | 43 | sprout G1 root ZHB |
| e) Diisopropyl-(5-dimethyl-amino)-2,3,7,8-tetrathianonane-1,9-dioate | 80 | 93 | 29 | 29 | sprout G1 root B |
| f) Hydrogenoxalate of e) | 100 | 87 | 43 | 43 | sprout G1B |
| g) (5-Dimethylamino-2,3,7,8-tetrathianonane-1,9-dioic-acid | 70 | 93 | 29 | 14 | sprout G1 root B |
| h) Dimethyl-(5-dimethyl-amino-5-methyl-2,3,7,8-tetrathianonane-1,9-dioate | | 100 | 50 | 43 | sprout G1 root B |
| i) Diethyl-(5-dimethyl-amino)-5-methyl-2,3,7,8-tetrathianonane-1,9-dioate | 100 | 80 | 0 | 0 | |
| j) Diethyl-5-(N-piperidino)-2,3,7,8-tetrathianonane-1,9-dioate | 100 | 87 | 43 | 38 | sprout G1A2 root B |
| k) Hydrogenoxalate of j) | 100 | 81 | 60 | 33 | sprout G1 |
| l) Dimethyl-5-(N-piperidino)-2,3,7,8-tetrathianonane-1,9-dioate | 130 | 100 | 0 | 0 | |
| m) Hydrogenoxalate of l) | 110 | 107 | 57 | 43 | sprout G1 root B |
| n) 5-(N-piperidino)-2,3,7,8-tetrathianone-1,9-dioic-acid | 80 | 87 | 43 | 29 | sprout G1 root HB |
| o) Dimethyl-5-(N-morpholino)-2,3,7,8-tetrathianonane-1,9-dioate | 70 | 107 | 43 | 57 | sprout G1 root B |
| p) Diethyl-5-(N-morpholino)-2,3,7,8-tetrathianonane-1,9-dioate | 50 | 87 | 29 | 38 | sprout G1A2 |
| q) Hydrogenoxalate of p) | 120 | 100 | 57 | 63 | sprout G1BA2 |
| r) Diisopropyl-5-(N-morpholino)-2,3,7,8-tetrathianonane-1,9-dioate | 90 | 107 | 29 | 43 | sprout G1 root B |
| s) 5-(N-morpholino)-2,3,7,8-tetrathianonane-1,9-dioic-acid | | 93 | 50 | 43 | sprout G1 |
| t) Dimethyl-5-(N-pyrrolidino)-2,3,7,8-tetrathianonane-1,9-dioate | 90 | 87 | 14 | 29 | sprout G1B root B |
| u) Diethyl-5-(N-pyrrolidino)-2,3,7,8-tetrathianonane-1,9-dioate | 90 | 107 | 43 | 29 | sprout G1B root B |
| v) Diisopropyl-5-(N-pyrrolidino)-2,3,7,8-tetrathianonane-1,9-dioate | 90 | 100 | 43 | 14 | sprout G1 root B |
| w) 5-Dimethylamino-2,3,7,8-tetrathianonane-1,9-dioic-N,N'-isopropylamide | 120 | 100 | 71 | 50 | sprout G1 |
| x) Diethyl-(6-dimethylamino- | | 60 | 17 | 24 | sprout G1 |

-continued

| Active agent of general formula I | Germination 1 | Sprout length in % Compared without untreated control plants after 7 | 7 days | Root length 7 | Other effects |
|---|---|---|---|---|---|
| 3,4,8,9-tetrathiaundecane-1,11-dioate | | | | | root B |
| y) Diisooctyl-(6-dimethyl-amino-3,4,8,9-tetrathia-undecane-1,11-dioate | 70 | 93 | 29 | 14 | sprout G1B root B |
| z) Diethyl-6-(N-morpholino)-3,4,8,9-tetrathiaundecane-1,11-dioate | | 87 | 33 | 29 | sprout G1 root B |

The abbreviations, used in column "other effects", signify:
G1 = inhibited growth of leaves
A = auxin effect: bendings, thickenings in the whole plant
A2 = auxin effect along the stems
B = burns
H = inhibited sprouting of lateral shoots or lateral roots
Z = destruction of final bud or main root vegetation point The active agents, referred to in Test A above as compounds (c), (d), (e), (f), (g), (h), (i), (j), (k), (l), (m), (n), (o), (p), (q), (s), (x), (y) and (z), particularly those of (c), (g) and (f), also exhibit a herbicidal effect under the conditions of the Test.

TEST B: Determination of germination rate and sprout growth in cress (*Lepidium sativum L*)

6 Plastics pots of 7 cm in diameter are filled with sterilized peat culture substrate and sand and then sprayed with 20 cc of spraying liquor at concentrations of (a) 8,000, (b) 4,000, (c) 2,000, (d) 1,000, (e) 500, (f) 250, (g) 125, (h) 62.5 p.p.m. of active agent of general formula I.

1 To 2 hours after treatment, 20 cress seeds are sown on the treated soil surface. The pots are transferred to climate cabinets and kept at 25° C under luminescent lighting (6000 to 8000 lux). After 21 days the germination rate and the longitudinal growth of the sprouts are determined. Other growth effects are visually determined in comparison with control plants. The activity index is indicated as follows:

$$\frac{\text{smallest herbicidal concentration}}{\text{smallest plant growth regulator concentration}}.$$

The results are set out in Table 2 below.

TABLE 2

| Active agent of general formula I | smallest herbicidal concentration in p.p.m. | smallest plant growth regulator concentration in p.p.m. | activity index |
|---|---|---|---|
| Dimethyl-(5-morpholino)-3,4,8,9-tetrathiasebacoate | 2000 | ≤ 62,5 | ≥ 32 |
| Diisooctyl-(6-dimethylamino)-3,4,8,9-tetrathiaundecane-1,11-dioate | 1000 | ≤ 62,5 | ≥ 16 |
| 5-Piperidino-2,3,7,8-tetrathianonane-1,9-dioic acid | 500 | ≤ 62,5 | ≥ 8 |
| Hydrogenoxalate of dimethyl-(5-dimethylamino)-2,3,7,8-tetrathianonane-1,9-dioate | 500 | ≤ 62,5 | ≥ 8 |

TABLE 2-continued

| Active agent of general formula I | smallest herbicidal concentration in p.p.m. | smallest plant growth regulator concentration in p.p.m. | activity index |
|---|---|---|---|
| 5-Dimethylamino-2,3,7,8-tetrathianonane-1,9-dioic acid | 500 | ≤ 62,5 | ≥ 8 |

TEST C: Defoliant test with cotton plants (*Gossypium hirsutum*) in the post-emergence process Culture flasks of 15 × 13 × 8 cm in diameter are filled with sterilized peat culture substrate and sand. 8 Cotton seeds are then sown on the soil surface and kept at 25° C for approximately 3 weeks. When the cotyledones are well developed, the number of the plants is reduced to 5 uniformly grown plants for each flask. 5 cc of a spraying liquor, containing (a) 8,000, (b) 4,000 and (c) 2,000 p.p.m. of active agent of general formula I, are sprayed on each vessel.

After 27 days, the percentage of the dropped cotyledones is visually determined in comparison with the untreated control plants.

The results are set out in Table 3 below.

TABLE 3

| Active agent of general formula I | Concentration | % of dropped cotyledones per 5 plants (control = 0) |
|---|---|---|
| Dimethyl-(5-morpholino)-2,3,7,-8-tetrathianonane-1,9-dioate | a | 100 |
| | b | 40 |
| | c | 30 |
| untreated | | 0 |

Of particular interest as plant growth regulators are the compounds of formula I, wherein $R_1$ and $R_2$, together with the nitrogen atoms to which they are bound form a heterocycle, notably the compounds of formula Ib,

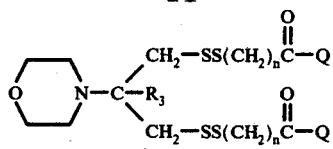

wherein $R_3$, Q and n are as defined above, particularly the compounds of formula Ib'

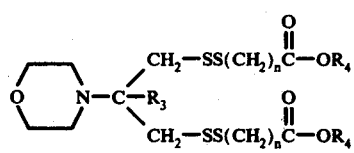

wherein $R_3$, $R_4$ and $n$ are as defined above, especially the compounds of formula Ib or Ib', wherein $n$ is 1 or 2.

Of particular interest as herbicides are the compounds of formula Ic,

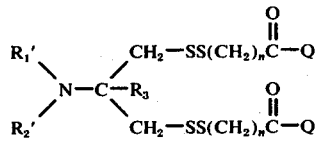

wherein $R_3$, Q and $n$ are as defined above and $R_1'$ and $R_2'$ are each, independently, alkyl ($C_1$–$C_5$), particularly the compounds of formula Ic',

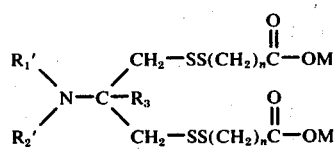

wherein $R_1'$, $R_2'$, $R_3$, M and $n$ are as defined above, especially the compounds of formulae Ic and Ic', wherein $n$ is 1 or 2.

In general, acid addition salt forms of the compounds of formula I exhibit the same order of activity as the free base forms.

The following Examples illustrate the production of the compounds of general formula I. All temperatures are indicated in degrees centigrade and all parts and percentages are by weight.

EXAMPLE 1:
Diethyl-(5-dimethylamino)-2,3,7,8-tetrathianonane-1,9-dioate

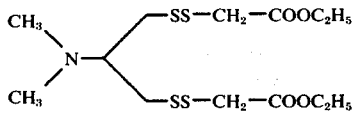

a)

45.9 g (0.1 mol) of 1,3-bis-(p-toluenesulphonylthio)-2-dimethylaminopropane are suspended in 200 cc of absolute methanol. A methanolic solution of 0.2 mol of the sodium salt of mercaptoethyl acetate, produced by dissolving 4.6 g (0.2 mol) of sodium in 100 cc of absolute methanol and adding 24.2 g (0.2 mol) of mercaptoethyl acetate, is added dropwise with stirring over the course of 2 hours, at room temperature. The reaction mixture is kept at room temperature for one further hour, heated to 50° and stirred for approximately one further hour. After cooling to room temperature, the precipitated potassium-p-toluenesulphinate is filtered off and the solvent evaporated in a vacuum. The residue is taken up in chloroform and washed twice with 100 cc amounts of water. The chloroform solution is dried with sodium sulphate and then evaporated in vacuum. The resulting oil may be liberated from the slightly volatile constituents by heating to 50° over the course of 30 minutes in a high vacuum.

| Analysis: | $C_{13}H_{25}NO_4S_4$ | Molecular weight: | | 387.6 |
|---|---|---|---|---|
| Calc. | C 41.3 % | H 6.5 % | N 3.6 % | S 33.1 % |
| Found | 41.6 % | 6.7 % | 3.7 % | 32.9 % |

EXAMPLE 2: Hydrogenoxalate of diethyl-(5-dimethylamino)-2,3,7,8-tetrathianonane-1,9-dioate 7.6 g (0.2 mol) of diethyl-(5-dimethylamino)-2,3,7,8-tetrathianonane-1,9-dioate are dissolved in 30 cc of absolute ethanol. A solution of 2 g (0.22 mol) of andydrous oxalic acid in 30 cc of absolute ether is added thereto. The precipitated hydrogenoxalate is suction filtered, washed with absolute ether and dried at 40° in a high vacuum. Colourless crystals, having a M.P. of 82°, are obtained.

| Analysis: | $C_{15}H_{27}NO_8S_4$ | Molecular weight: | | 477.6 |
|---|---|---|---|---|
| Calc. | C 37.7 % | H 5.7 % | N 2.9 % | S 26.9 % |
| Found | 36.8 % | 5.5 % | 3.0 % | 26.5 % |

EXAMPLE 3:
(5-Dimethylamino)-2,3,7,8-tetrathianonane-1,9-dioic acid

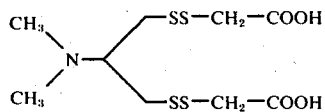

10 g (0.026 mol) of diethyl-(5-dimethylamino)-2,3,7,8-tetrathianonane-1,9-dioate produced in accordance with Example 1, are added to 100 cc of 1N sulphuric acid and the mixture is stirred at 100° until a clear solution is obtained (approximately 4 to 5 hours). After cooling, the reaction solution is neutralized with 100 cc of 1N sodium hydroxide solution and evaporated to dryness in a vacuum. The dry residue is extracted with 150 cc of absolute methanol. After evaporation in a vacuum, then in a high vacuum at 50°, a slightly coloured glassy mass is obtained from the methanol.

| Analysis: | $C_9H_{17}NO_4S_4$ | Molecular weight: | | 331.5 |
|---|---|---|---|---|
| Calc. | C 32.6 % | H 5.2 % | N 4.2 % | S 38.7 % |
| Found | 32.2 % | 5.2 % | 4.0 % | 38.4 % |

EXAMPLE 4:
Dimethyl-(5-dimethylamino-5-methyl)-2,3,7,8-tetrathianonane-1,9-dioate

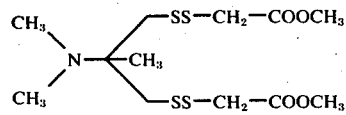

23.6 g (0.05 mol) of 1,3-bis-(p-toluenesulphonylthio)-2-dimethylamino-2-methylpropane are suspended in 200 cc of absolute methanol. A methanolic solution of 0.11 mol of the sodium salt of the mercaptomethyl acetate, — produced by dissolving 2.5 g (0.11 mol) of sodium in 100 cc of absolute methanol and adding 11.7 g (0.11 mol) of mercaptomethyl acetate, — is added dropwise with stirring to the suspension at room temperature over the course of 2 hours. The reaction mixture is kept at room temperature for one further hour, then heated to 50° and stirred for approximately one further hour. After cooling to room temperature, the precipitated potassium-p-toluenesulphinate is filtered off and the solvent is evaporated in a vacuum. The residue is taken up in chloroform and washed twice with 100 cc amounts of water. The chloroform solution is dried with sodium sulphate and then evaporated in a vacuum.

The resulting oil may be liberated from the slightly volatile constituents by heating to 50° over the course of 30 minutes in a high vacuum.

| Analysis: | $C_{12}H_{23}NO_4S_4$ | Molecular weight: | | 373.6 |
|---|---|---|---|---|
| Calc. | C 38.6 % | H 6.2 % | N 3.7 % | S 34.3 % |
| Found | 39.1 % | 6.3 % | 3.5 % | 33.9 % |

EXAMPLE 5: Hydrogenoxalate of dimethyl-(5-piperidino)-2,3,7,8-tetrathianonane-1,9-dioate

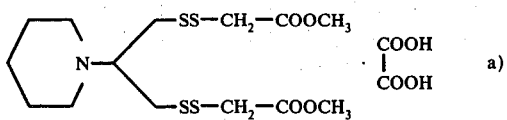

36 g (0.072 mol) of 1,3-bis-(p-toluene-sulphonylthio)-2-piperidinopropane are suspended in 200 cc of absolute methanol. A methanolic solution of 0.144 mol of the sodium salt of mercaptomethyl acetate, produced by dissolving 3.3 g (0.144 mol) of sodium in 100 cc of absolute methanol and adding 15.3 g (0.144 mol) of mercaptomethyl acetate, is added dropwise with stirring at room temperature over the course of 2 hours. The reaction is kept at room temperature for one further hour, heated to 50° and stirred for approximately one further hour. After cooling to room temperature, the precipitated potassium-p-toluenesulphinate is filtered off and the solvent evaporated in a vacuum. The residue is taken up in chloroform and washed twice with 100 cc amounts of water. The chloroform solution is dried with sodium sulphate and then evaporated in a vacuum. A viscous oil is obtained.

The hydrogenoxalate is produced by dissolving 8 g of the obtained oil in 30 cc of absolute ether and adding thereto a solution of 2 g of anhydrous oxalic acid in 30 cc of absolute ether. The precipitated hydrogenoxalate is suction filtered, washed with absolute ether and dried at 40° in a high vacuum.

Colourless crystals, having a M.P. of 183°–185°, are obtained.

| Analysis: | $C_{16}H_{27}NO_8S_4$ | Molecular weight: | | 489.6 |
|---|---|---|---|---|
| Calc. | C 39.2 % | H 5.6 % | N 2.9 % | S 26.2 % |
| Found | 40.1 % | 5.8 % | 3.1 % | 25.9 % |

EXAMPLE 6:
Dioctyl-(6-dimethylamino)-3,4,8,9-tetrathiaundecane-1,11-dioate

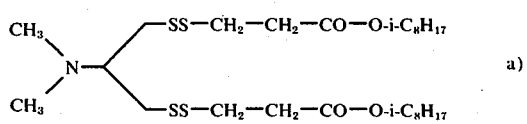

45.9 g (0.1 mol) of 1,3-bis-(p-toluenesulphonylthio)-2-dimethylaminopropane are suspended in 200 cc of absolute methanol. A methanolic solution of 0.2 mol of the sodium salt of the isooctyl 3-mercaptopropionic acid, produced by dissolving 4.6 g (0.2 mol) of sodium in 100 cc of absolute methanol and adding 43.6 g (0.2 mol) of isooctyl 3-mercaptopropionic acid, is added dropwise with stirring at room temperature over the course of 2 hours. The reaction mixture is kept at room temperature for one further hour, heated to 50° and stirred for approximately one further hour. After cooling to room temperature, the precipitated potassium-p-toluenesulphinate is filtered off and the solvent evaporated in a vacuum. The residue is taken up in chloroform and washed twice with 100 cc amounts of water. The chloroform solution is dried with sodium sulphate and then evaporated in a vacuum.

The resulting oil may be liberated from the slightly volatile constituents by heating to 50° over the course of 30 minutes in a high vacuum.

| Analysis: | $C_{27}H_{53}NO_4S_4$ Molecular weight: | | | 584 |
|---|---|---|---|---|
| Calc. | C 55.5 % | H 9.1 % | N 2.4 % | S 22.0 % |
| Found | 54.9 % | 8.8 % | 2.4 % | 21.8 % |

EXAMPLE 7:
5-Dimethylamino-2,3,7,8-tetrathianonane-1,9-dioic di-N,N'-isopropylamide

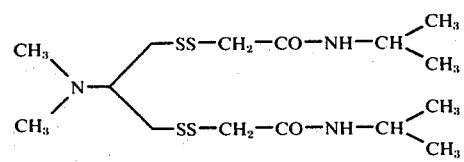

23 g (0.05 mol) of 1,3-bis-(p-toluenesulphonylthio)-2-dimethylaminopropane are suspended in 300 cc of absolute acetonitrile. A suspension of 0.11 mol of the sodium salt of the mercaptoacetic isopropylamide, produced by boiling 17.5 g (0.11 mol) of acetylthioacetic isopropylamide in 300 cc of absolute acetonitrile for 4 hours and adding 6.0 g (0.11 mol) of sodium methylate, is added dropwise with stirring at room temperature over the course of 2 hours. The reaction mixture is kept at room temperature for one further hour, heated to 50° and stirred for approximately one further hour. After cooling to room temperature, the precipitated potassium-p-toluenesulphinate is filtered off and the solvent evaporated in a vacuum. The residue is taken up in chloroform and washed twice with 100 cc amounts of water. The chloroform solution is dried with sodium sulphate and then evaporated in a vacuum. The residue is recrystallized from acetic ester and colourless crystals, having a M.P. of 114°, are obtained.

| Analysis: | $C_{15}H_{31}N_3O_2S_4$ Molecular weight: | | | 413.7 |
|---|---|---|---|---|
| Calc. | C 43.6 % | H 7.6 % | N 10.2 % | S 31.0 % |
| Found | 43.8 % | 7.5 % | 10.4 % | 30.6 % |

The compounds of general formula I, indicated in the following Table, may be produced in manner analogous to that described in Examples 1 to 7.

| Example No. | $R_1$ | $R_2$ | $R_3$ | Q | n | Salt | Empirical formula Molecular weight | Analysis Calc. Found C | H | N | S | M.P. |
|---|---|---|---|---|---|---|---|---|---|---|---|---|
| 8 | $CH_3$ | $CH_3$ | H | $-OCH_3$ | 1 | — | $C_{11}H_{21}NO_4S$ 359,5 | 36,7 36,3 | 5,9 5,8 | 3,9 3,4 | 35,7 34,9 | |
| 9 | $CH_3$ | $CH_3$ | H | $-OCH_3$ | 1 | Hydrogen-oxalate | $C_{11}H_{21}NO_4S_4 \cdot C_2H_2O_4$ 449,6 | 34,7 34,8 | 5,2 5,2 | 3,1 3,6 | 28,5 29,0 | 77–78° |
| 10 | $CH_3$ | $CH_3$ | H | $-O-i-C_3H_7$ | 1 | — | $C_{15}H_{21}NO_4S_4$ 415,7 | 43,3 43,2 | 7,0 7,0 | 3,4 3,2 | 30,9 30,4 | |
| 11 | $CH_3$ | $CH_3$ | H | $-O-i-C_3H_7$ | 1 | Hydrogen-oxalate | $C_{15}H_{21}NO_4S_4 \cdot C_2H_5O_5$ 505,7 | 40,4 39,7 | 6,2 5,9 | 2,8 3,0 | 25,4 25,8 | 165° |
| 12 | $CH_3$ | $CH_3$ | $CH_3$ | $-OC_2H_5$ | 1 | — | $C_{15}H_{27}NO_4S_4$ 401,7 | 41,9 41,2 | 6,8 6,4 | 3,5 3,5 | 31,9 32,4 | |
| 13 | N-Piperidino | | H | $-OC_2H_5$ | 1 | — | $C_{16}H_{29}NO_4S_4$ 427,7 | 44,9 43,8 | 6,8 6,6 | 3,3 3,5 | 30,0 30,6 | |
| 14 | N-Piperidino | | H | $-OC_2H_5$ | 1 | Hydrogen-oxalate | $C_{16}H_{29}NO_4S_4 \cdot C_2H_2O_4$ 517,7 | 41,8 42,3 | 6,0 6,0 | 2,7 2,9 | 24,8 23,9 | 178–180° |
| 15 | N-Piperidino | | H | $-OH$ | 1 | — | $C_{12}H_{21}NO_4S_4$ 371,6 | 38,8 37,9 | 5,7 6,0 | 3,8 3,6 | 34,5 34,2 | |
| 16 | N-Piperidino | | H | $-OCH_3$ | 1 | — | $C_{14}H_{25}NO_4S_4$ 399,6 | 42,1 42,3 | 6,3 6,2 | 3,5 3,2 | 32,1 31,8 | |
| 17 | N-Morpholino | | H | $-OC_2H_5$ | 1 | — | $C_{15}H_{27}NO_5S_4$ 429,6 | 41,9 41,0 | 6,3 6,2 | 3,3 3,4 | 29,9 30,9 | |
| 18 | N-Morpholino | | H | $-OC_2H_5$ | 1 | Hydrogen-oxalate | $C_{15}H_{27}NO_5S_4 \cdot C_2H_2O_4$ 519,6 | 39,3 39,1 | 5,6 5,5 | 2,7 2,9 | 24,7 23,8 | 191° |
| 19 | N-Morpholino | | H | $-OCH_3$ | 1 | — | $C_{13}H_{23}NO_5S_4$ 401,6 | 38,9 39,2 | 5,8 5,9 | 3,5 3,7 | 31,9 31,2 | |
| 20 | N-Morpholino | | H | OH | 1 | — | $C_{11}H_{19}NO_5S_4$ 373,5 | 35,4 34,8 | 5,1 5,2 | 3,7 3,2 | 34,3 33,8 | |
| 21 | N-Morpholino | | H | $-O-i-C_3H_7$ | 1 | — | $C_{17}H_{31}NO_5S_4$ 457,7 | 44,6 44,7 | 6,8 6,8 | 3,1 3,0 | 28,0 27,1 | |
| 22 | N-Pyrrolidino | | H | $-OC_2H_5$ | 1 | — | $C_{15}H_{27}NO_4S_4$ 413,6 | 43,6 42,8 | 6,6 6,4 | 3,4 3,4 | 31,0 31,5 | |
| 23 | N-Pyrrolidino | | H | $-OCH_3$ | 1 | — | $C_{13}H_{23}NO_4S_4$ 385 | 40,5 39,5 | 6,0 5,9 | 3,6 3,5 | 33,3 32,8 | |
| 24 | N-Pyrrolidino | | H | $-O-i-C_3H_7$ | 1 | — | $C_{17}H_{31}NO_4S_4$ 441 | 46,2 46,2 | 7,1 6,9 | 3,2 3,2 | 29,0 29,6 | |
| 25 | N-Pyrrolidino | | H | $-O-i-C_3H_7$ | 1 | Hydrogen-oxalate | $C_{17}H_{31}NO_4S_4 \cdot C_2H_2O_4$ 531,7 | 42,9 41,9 | 6,3 6,0 | 2,6 3,0 | 24,1 23,8 | 181° |
| 26 | $CH_3$ | $CH_3$ | H | $-OC_2H_5$ | 2 | — | $C_{15}H_{29}NO_4S_4$ 415,7 | 43,3 43,8 | 7,0 7,0 | 3,4 3,5 | 30,9 30,2 | |
| 27 | N-Morpholino | | H | $-OC_2H_5$ | 2 | — | $C_{17}H_{31}NO_5S_4$ 457,7 | 44,6 45,1 | 6,8 6,8 | 3,1 2,8 | 28,0 26,7 | |

What is claimed is:
1. A compound of the formula:

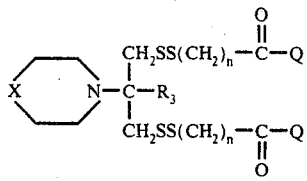

wherein X is oxygen, —NH—, —CH₂— or a direct covalent bond,
$R_3$ is hydrogen or $C_1$ or $C_2$ alkyl,
$n$ is 1, 2 or 3,
Q is —OM, —OR$_4$ or —NR$_5$R$_6$,
M is hydrogen, an alkali metal cation or the ammonium cation,
$R_4$ is $C_1$ to $C_8$ alkyl, phenyl or phenyl mono-, di- or tri-substituted independently by fluoro, chloro, bromo, $C_1$ to $C_5$ alkoxy, phenoxy, carboxy, $C_2$ to $C_6$ alkoxycarbonyl or carboxamido,
$R_5$ is hydrogen, $C_1$ to $C_5$ alkyl, phenyl or phenyl mono-, di- or tri-substituted independently by fluoro, chloro, bromo, nitro, $C_1$ to $C_5$ alkoxy, phenoxy, carboxy, $C_2$ to $C_6$ alkoxycarbonyl or carboxamido,
$R_6$ is —NHR$_7$ or independently $R_5$, and
$R_7$ is hydrogen or $C_1$ to $C_5$ alkyl,
or an acid addition salt thereof.

2. A compound of claim 1, of the formula:

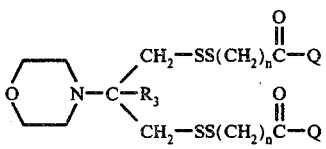

wherein $R_3$, Q and $n$ are as defined in claim 1.

3. A compound of claim 2, of the formula:

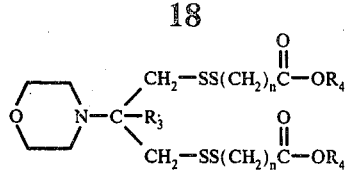

wherein $R_3$, $R_4$ and $n$ are as defined in claim 2.

4. A compound according to claim 1, wherein $n$ is 1 or 2.

5. The compound of claim 1, which is dimethyl(5-piperidino)-2,3,7,8-tetrathianonane-1,9-dioate.

6. The compound of claim 1, which is dimethyl(5-piperidino)-2,3,7,8-tetrathianonane-1,9-dioate in hydrogen oxalate form.

7. The compound of claim 1, which is diethyl(5-piperidino)-2,3,7,8-tetrathianonane-1,9-dioate.

8. The compound of claim 1, which is diethyl(5-piperidino)-2,3,7,8-tetrathianonane-1,9-dioate in hydrogen oxalate form.

9. The compound of claim 1, which is 5-piperidino-2,3,7,8-tetrathianonane-1,9-dioic acid.

10. The compound of claim 3, which is diethyl(5-morpholino)-2,3,7,8-tetrathianonane-1,9-dioate.

11. The compound of claim 3, which is diethyl(5-morpholino)-2,3,7,8-tetrathianonane-1,9-dioate in hydrogen oxalate form.

12. The compound of claim 3, which is dimethyl(5-morpholino)-2,3,7,8-tetrathianonane-1,9-dioate.

13. The compound of claim 2, which is 5-morpholino-2,3,7,8-tetrathianonane-1,9-dioic acid.

14. The compound of claim 3, which is di-isopropyl-(5-morpholino)-2,3,7,8-tetrathianonane-1,9-dioate.

15. The compound of claim 1, which is diethyl(5-pyrrolidino)-2,3,7,8-tetrathianonane-1,9-dioate.

16. The compound of claim 1, which is dimethyl(5-pyrrolidino)-2,3,7,8-tetrathianonane-1,9-dioate.

17. The compound of claim 1, which is di-isopropyl-(5-pyrrolidino)-2,3,7,8-tetrathianonane-1,9-dioate.

18. The compound of claim 1, which is di-isopropyl-(5-pyrrolidino)-2,3,7,8-tetrathianonane-1,9-dioate in hydrogen oxalate form.

19. The compound of claim 3, which is diethyl(6-morpholino)-3,4,8,9-tetrathiaundecane-1,11-dioate.

* * * * *